US00PP15662P2

(12) United States Plant Patent
Davidson

(10) Patent No.: US PP15,662 P2
(45) Date of Patent: Mar. 15, 2005

(54) FLORABUNDA ROSE NAMED 'HADBAL'

(50) Latin Name: *Rosa hybrida*
Varietal Denomination: Hadbal

(76) Inventor: Harvey Daniel Davidson, 3 El Verano Rd., Orinda, CA (US) 94563

( * ) Notice: Subject to any disclaimer, the term of this patent is extended or adjusted under 35 U.S.C. 154(b) by 5 days.

(21) Appl. No.: 10/724,478

(22) Filed: Dec. 1, 2003

(51) Int. Cl.[7] ..... A01H 5/00
(52) U.S. Cl. ..... Plt./143
(58) Field of Search ..... Plt./143

*Primary Examiner*—Bruce R. Campell
*Assistant Examiner*—S. B. McCormick-Ewoldt

(57) ABSTRACT

A new and distinct rose cultivar of the Florabunda class characterized by: having stems without prickles; white stripes lightly scattered on pink flowers; clusters of three to six flowers; very rapid rebloom cycle; upright bushy plants of medium height; being well covered with medium green matte foliage; with excellent resistance to powdery and downy mildew, rust and blackspot.

The generic name of this plant is designated as 'Hadbal'. It is being marketed under the commercial name of 'Smooth Ballerina'.

1 Drawing Sheet

Botanical/commercial classification: *Rosa hybrida*/Floribunda Rose Plant: var. 'Hadbal'.

SPECIFICATION

The present invention relates to a new and distinctive cultivar of rose plant of the Florabunda class, which was originated by my crossing 'Pink Empress' as the seed parent with the unnamed seedling '(Blue Moon×Roller Coaster)' as the pollen parent. The observations herein stated were made of the original seven year old plant during the year 2003. Pollination (June, 96); the period of embryo maturation; stratification at 39 degrees F. for 90 days; and germination (February 97) were performed in Orinda, Calif.

Among the novel characteristics possessed by the new cultivar which distinguish it from:

(a) All other cultivars of which I am aware are:
- (1) Prickles being absent from any stems.
- (2) White stripes lightly scattered on pink flowers.
- (3) Flowers in clusters of 3 to 6 blooms.
- (4) Very consistent free bloomer.
- (5) Bushy, upright plant, covered with medium green matte foliage.
- (6) Very resistant to powdery and downy mildew, rust and blackspot.

(b) Seed parent: Pink hybrid tea having prickles.

Pollen parent: Striped white on red, tall florabunda with prickles. Asexual reproduction of the new *rose* cultivar by budding onto the rootstock 'Dr. Huey', as performed at Wasco, Calif., shows that the aforementioned and all other distinctive characteristics come true to form and are established and transmitted through succeeding propagations.

The accompanying photograph shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers such as: 'Yellow Group 16A' in Fan 1 of The Royal Horticultural Society Colour Chart.

Parentage:

*Seed parent.*—IRAR registered: 'HADEMP'; commercial name: 'Pink Empress', U.S. Plant Patent — None.

*Pollen parent.*—Seedling — '(Blue Moon× Rollercoaster)'.

The following observations were made of the original plant 'Hadbal' grown outdoors, in Orinda, Contra Costa County, Calif.

Inflorescense:

Blooming habit of flower:

A. Bud:
- (*1*) *Size.*—Sepals enclosed, 16–20 mm from base of sepals to top of bud.
- (*2*) *Form.*—Ovoid; Diameter: mature bud, sepals enclosed — 16 to 20 mm.
- (*3*) *Sepals.*—28 to 30 mm in length; 8 to 10 mm extension beyond bud; no serration shown on sepal edges. Generally 3 out of 5 sepals show appendages on each side, 2 to 3 mm length. Sepals show glandular development on edges. Heavy cotton matting on inner surface, fine matting on outer surfaces. Outside color: near to Yellow Green 146B with slight shadings of Greyed Red Group 181B; inside: Greyed Green Group 196B.
- (*4*) *Peduncle.*—Length — 6 to 8 cm. Surface — smooth, some fine hairs, a few glandular hairs, no prickles. Strength — firm. Color — near Yel. Green 146C with shades of Greyed Red Group 181B.
- (*5*) *Receptacle.*—Shape — Oblong, 6–8 mm diameter, Color — same peduncle.
- (*6*) *Color.*—When sepals first divide, outside bud petals with shadings near to Red Group 47B, 50B and 50C.

B. Bloom:
- (*1*) *Size.*—When open — 8 to 9 cm.
- (*2*) *Borne.*—per stem clusters of 3 up to 6 per stem.
- (*3*) *Form.*—Globular.

(*4*) *Petalage.*—Average — 48 to 52.

(*5*) *Color.*—Early open: outside petals with mixed shadings near to Red. Purple Group 68A, B, C, D including some scattered stripes of White Group 155D; inside petals with same shadings of Red Purple Group 68A, B, C and D, fewer stripings of White Group 155D are noted. Aging petals similar to earlier stages with increasing of 68A, B.

C. Petals:

(*1*) *Texture.*—Smooth; Substance: Firm.

(*2*) *Form.*—Slightly ruffled; wedge shaped; rarely curled at apex.

(*3*) *Arrangement.*—Semi-regular.

(*4*) *Mature size.*—Average length: 3.5–4 cm; Average width: 3–3.5 cm.

(*5*) *Center petaloids.*—Average 6 to 10. Length: 8–20 mm; Width: 5–12 mm; Color: Shadings of Red Purple Grp. 68A, B, C and D.

(*6*) *Persistance.*—Holds well; petals drop cleanly at end of bloom.

(*7*) *Fragrance.*—Moderate.

(*8*) *Lasting quality.*—On bush: 6–8 days; cut 4–5 days.

REPRODUCTIVE ORGANS

A. Stamen:

(*1*) *Arrangement.*—Regular around styles.

(*2*) *Number.*—Average — 52–58.

(*3*) *Length.*—Average — 3 to 7 mm.

(*4*) *Filaments.*—Color — Close to Red Purple Grp. 62B.

(*5*) *Anthers.*—Color — Yel. Orange Grp. 22A.

(*6*) *Pollen.*—Color — Same as (5).

B. Pistil:

(*1*) *Styles.*—Length: 5–13 mm from center of ovary; number 66–74; color: near to Red Purple Grp. 62C; coated with white hairs.

(*2*) *Stigma.*—Color — Close to Yel. Orange Grp. 22C.

(*3*) *Ovary.*—Shape — oblong; 5–7 mm center cross section at sepal base.

C. Hips: Sets seed. Mature hip: Size: 1½–2 cm; Shape: Round. Color: Yel. Green 146B with shades near to Red Group 44D.

PLANT

A. Form: Upright.

B. Growth: Vigorous, Height: average 1 m; Width: average 50 cm.

C. Stem length: Basal break to flower bud tip: average 90–100 cm.

D. Foliage: Compound of 3 to 5 leaflets on bloom stem; 5 to 7 leaflets on main canes.

(*1*) *Quantity.*—Stems well covered.

(*2*) *Color.*—New foliage: Upper side near to Yel. Green 146B with slight shading of Greyed Orange 176C on leaf edges; under side near to Yel. Green 146C. Old foliage: Upper side near to Yel. Green 147A; under side near to Yel. Green 146B.

(*3*) *Shape.*—Mature 5 leaflet: Length: stipule base to tip of leaflet — 11–12 cm. Center end leaflet: Oval and pointed; Length: 4½–5½ cm, width: 2½–3 cm.

(*4*) *Texture.*—Firm, leathery, matte finish.

(*5*) *Edge.*—Serration on outer edge. Average 4 to 5 points per 1 cm, with up to 1½ mm peak.

(*6*) *Rachis.*—Glandular hairs on upper side; none on lower side; few small prickles on lower side ½–1 mm length.

(*7*) *Stipules.*—Length 14–16 mm; auricle to 3–4 mm. Edge of stipule to tip of auricle with many glandular hairs.

E. Resistance to disease: Powdery and downy mildew, rust and blackspot: Excellent.

F. Wood: New wood — Color close to Yel. Green 146C; shadings near to Greyed Orange Group 172B; Bark — smooth. Old wood — Color close to Yel. Green 146B; Bark — smooth.

G. Prickles: None.

H. Winter hardiness: Average.

I claim:

1. A new and distinct rose cultivar of the Floribunda class with essential features as follows:

1. Prickles are absent from any stems.
2. White stripes lightly scattered on pink flowers.
3. Blooms in clusters of three to six flowers.
4. Very consistent free bloomer.
5. Bushy, upright plant, covered with medium green matte foliage.
6. Very resistent to powdery and downy mildew, rust and blackspot, substantially as shown herein and described.

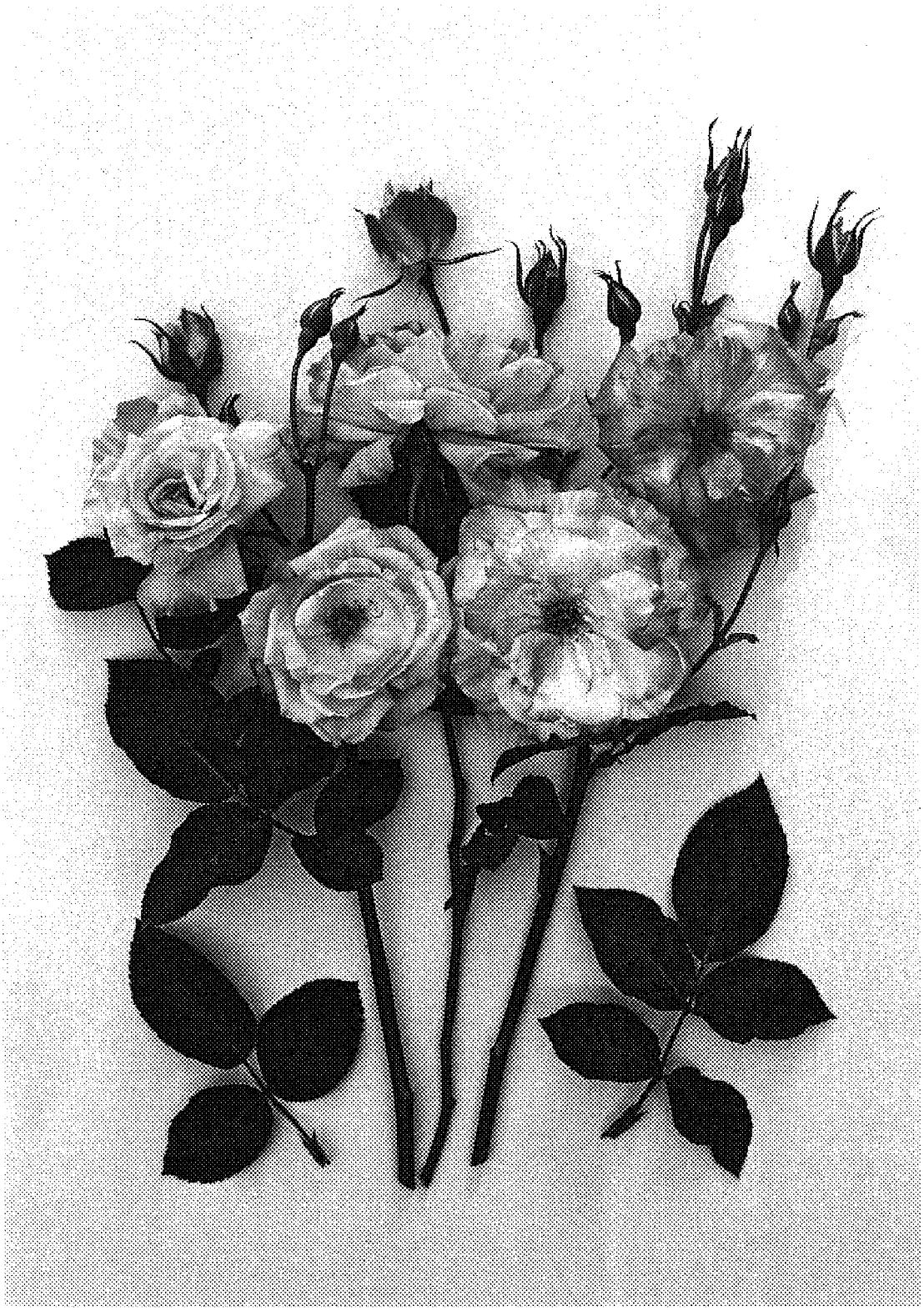

* * * * *